(12) United States Patent
DeSanto

(10) Patent No.: US 8,183,198 B2
(45) Date of Patent: May 22, 2012

(54) RHAMNOLIPID-BASED FORMULATIONS

(75) Inventor: Keith DeSanto, St. Petersburg, FL (US)

(73) Assignee: Rhamnolipid, IP, Inc

( * ) Notice: Subject to any disclaimer, the term of this patent is extended or adjusted under 35 U.S.C. 154(b) by 0 days.

(21) Appl. No.: 13/179,755

(22) Filed: Jul. 11, 2011

(65) Prior Publication Data
US 2011/0270207 A1  Nov. 3, 2011

Related U.S. Application Data

(62) Division of application No. 11/881,271, filed on Jul. 26, 2007, now Pat. No. 7,985,722.

(60) Provisional application No. 60/864,735, filed on Nov. 7, 2006, provisional application No. 60/822,461, filed on Aug. 15, 2006, provisional application No. 60/820,528, filed on Jul. 27, 2006.

(51) Int. Cl.
*C11D 3/22* (2006.01)

(52) U.S. Cl. ........ 510/470; 510/235; 510/238; 510/364; 510/365; 510/432; 510/511

(58) Field of Classification Search .......... 510/235, 510/238, 364, 365, 432, 470, 511
See application file for complete search history.

(56) References Cited

U.S. PATENT DOCUMENTS

| | | | | |
|---|---|---|---|---|
| 4,999,195 A | * | 3/1991 | Hayes | 424/114 |
| 5,520,839 A | * | 5/1996 | Hall et al. | 510/356 |
| 5,866,376 A | * | 2/1999 | Rocha et al. | 435/74 |
| 2003/0134783 A1 | * | 7/2003 | Harshey et al. | 514/9 |
| 2004/0120911 A1 | * | 6/2004 | Shah et al. | 424/70.11 |
| 2004/0152613 A1 | * | 8/2004 | Develter et al. | 510/421 |
| 2005/0266036 A1 | * | 12/2005 | Awada et al. | 424/405 |

* cited by examiner

*Primary Examiner* — Charles Boyer
(74) *Attorney, Agent, or Firm* — Defillo & Associates, Inc.; Evelyn A. Defilló

(57) ABSTRACT

The present invention relates to rhamnolipid-based formulations to clean, disinfect, deodorize, and act as an antimicrobial and antifungal agent for living and working environments. In addition, the present invention relates to the use of rhamnolipids to create a bio-film when applied to a surface, which prevents the growth of bacteria and fungus. This technique is especially useful to create clean surface areas for medical procedures, chemical testing, during food preparation, as well as for daycare centers and hospitals.

3 Claims, No Drawings

RHAMNOLIPID-BASED FORMULATIONS

REFERENCE TO RELATED APPLICATIONS

This is a divisional of U.S. patent application Ser. No. 11/881,271 filed on Jul. 26, 2007, now U.S. Pat. No. 7,985,722, which is a non-provisional of Provisional Application No. 60/820,528 filed Jul. 27, 2006; U.S. Provisional application No. 60/822,461 filed Aug. 15, 2006; and U.S. Provisional application No. 60/864,735 filed Nov. 7, 2006.

FIELD OF THE INVENTION

The present invention relates to rhamnolipid-based formulations. More specifically, it relates to formulations containing crude and/or purified rhamnolipids for household, industrial, medical, animal, and human use.

BACKGROUND OF THE INVENTION

Surfactants are chemicals that reduce the surface tension of water. A surfactant is made up of two parts, a head and a tail, each part exhibits differing properties: the head is hydrophilic (it is attracted to water), while the tail is hydrophobic (it tends to distance itself from water). Because of these characteristics, a surfactant exhibits a unique reaction when in contact with water, reducing the surface tension of water.

It is well known in the prior art that surfactants are used in the manufacture of soaps, laundry detergents, dishwashing liquids, personal care products, lubricants, emulsion polymerization, textile processing, mining flocculates, petroleum recovery, and wastewater treatment.

The majority of the surfactants used by the prior art are derived from petroleum sources. These chemical surfactants pose significant environmental risks because they form harmful compounds from incomplete biodegradation in water or soil.

In recent years, the prior art is showing an increase in the use of bio-surfactants, because they are an environmentally friendly alternative to petroleum-derived surfactants and their potential use in different areas, such as the food industry, agriculture, pharmaceuticals, cosmetic, and oil industries.

Rhamnolipid bio-surfactant secreted from *Pseudomonas Aeruginosa*, is a naturally occurring extracellular glycolipid that is found in the soil and on plants. Rhamnolipids are powerful bio-surfactants that provide a great antibacterial and antifungal activity, and low toxicity levels, which make them an attractive alternative to the known petroleum derived surfactant used in the pharmaceutical industry, the petroleum industry, agriculture, personal care products, animal cleaning products, and other applications.

In previous patents owned by the present assignee, rhamnolipids have been used basically in the medical field to combat certain types of bacteria, viruses, and fungi. The present inventor thought of the necessity of expanding the use of rhamnolipids to other fields.

The present inventor noticed that maintaining the cleanliness of non-human animals, which is particularly desirable when the animals live in close proximity to humans, or needs to be cleaned as part of the slaughter of animals for food preparation, or for cleaning the animals for dairy production, is often problematic. Without proper cleaning, the skin and fur of animals become soiled with an unkempt appearance, and unpleasant odors caused by bacteria can develop. Also, animals are subject to dryness or flaking of the skin, irritation caused by flea bites or other insect stings, sunburn, and various other irritations. Bathing animals, such as dogs, is tedious and time consuming, and can be traumatic for the animal. Bathing animals, such as cats, can be an arduous undertaking. For larger animals (e.g. horses, cattle, or animals that are confined in zoos) attempts to improve and maintain a clean appearance of the fur, hair, hide, and skin by conventional means (e.g. bathing) is challenging and often impossible.

The present inventor thought of the necessity of finding a solution to the above-identified problem by simplifying the process of cleaning and maintaining the appearance of animal fur, hair, hide, and skin in a facile manner, and at the same time clean and deodorize the skin and fur of animals without having all the hazards of bathing the animal.

Furthermore, the present inventor focused his attention on the problems presented by the existing personal cleaning products for humans. It was noticed that some personal cleaning products contain compounds that can damage clothes, and also, the products fail to contain antibacterial or antimicrobial agents that prevent the growth of bacteria that causes unpleasant smells and skin irritations.

In addition, the present inventor noticed that some soaps, shampoos, skin lotion, and personal wipes on the market generally offer cleaning abilities, however most of them fail to contain antibacterial agents that are non-toxic, biodegradable, and environmentally friendly.

The present inventor thought of the necessity of finding a solution to the above-identified problem by providing a personal cleaning solution that offers cleaning abilities, along with antibacterial capabilities, while at the same time is non-toxic, biodegradable, and environmentally friendly.

Then, the present inventor focused his attention to the problems presented when cleaning and disinfecting a surface or room where medical procedures or chemical testing are performed, food preparation is conducted, as well as for daycare centers and hospitals. It was noticed that the majority of the existing cleaning solutions do not contain an antibacterial or antimicrobial agent that offers cleaning abilities, along with antibacterial capabilities, while at the same time is non-toxic, biodegradable, and environmentally friendly.

SUMMARY OF THE INVENTION

It is an objective of the present invention to provide a formulation that simplifies the processes of cleaning and maintaining the appearance of animal fur, hair, hide, and skin in a facile manner, and at the same time clean and deodorize the skin and fur of animals without the hazards of bathing the animal.

It is an objective of the present invention to provide a formulation that can be use on medical applications such as wound healing to all animals.

It is another objective of the present invention to provide a personal cleaning formulation that offers cleaning abilities, along with antibacterial capabilities, while at the same time is non-toxic, biodegradable, and environmentally friendly.

It is another objective of the present invention to provide a cleaning formulation that contains an antibacterial or antimicrobial agent that offers cleaning abilities, along with antibacterial capabilities, while at the same time is non-toxic, biodegradable, and environmentally friendly.

After intense research and development, the present inventor discovered that rhamnolipids can be used to clean, disinfect, deodorize, and act as an antimicrobial and an antifungal agent for living and working environments. In addition, the present inventor discovered that rhamnolipids can also be used in cleaning solutions for humans and animals.

In addition, the present inventor discovered that rhamnolipids are also able to create a bio-film when applied to a surface, which prevents the growth of bacteria and fungus. This technique is especially useful to create clean surface areas for medical procedures, chemical testing, during food preparation, as well as for daycare centers and hospitals. This same coating can be applied to medical devices, bandages, and other wound care appliances.

The formulations of the present invention present good antibacterial, antifungal, emulsification, wetting, detergency, and foaming properties, along with low toxicity. They are environmentally friendly and do not produce any harmful degradation products.

The rhamnolipid formulation according to the present invention comprises:
0.01% to 99.9% of rhamnolipid; and
the balance being a carrier.
Preferably 0.01% to 70% of rhamnolipid.

The carrier may be chosen from: polyethylene glycol (PEG), citric acid, water, sodium laureth sulfate, aloe, alcohol, glycerin, canola oil, petrolatum, sodium hydroxide, glyceril stearate, potassium hydroxide, mineral oil, lanolin, stearic acid, glycol stearate, sodium chloride, cocoa butter, citric acid, sodium phosphate, xanthan gum, potassium laureth phosphate, poysorbate 20, Vitamin E, wax, silica, cyclopenta Siloxane, titanium dioxide, propylene glycol, stedric acid, talc, or a combination thereof.

In a preferable embodiment, the present invention uses polyethylene glycol (PEG) as a carrier. PEG is water-soluble, comes in different molecular weights (and viscosities) and can be chemically "decorated" or modified to alter its hydrophilicity.

In another preferable embodiment of the present invention the rhamnolipid is a crude or partial purified rhamnolipid containing a mono-rhamnolipid and a di-rhamnolipid, or mixture of both. In another embodiment, the present invention contemplates the use of highly purified rhamnolipids.

The formulation is a pet cleaning formulation, a personal cleaning formulation, a household cleaning formulation, a aerosol or nebulizer mist, a surface cleaning formulation, foam, or coating.

In addition, the formulation of the present invention can be incorporated into a shampoo base, an animal cleaning solution base, a detergent base, a fabric or non-fabric substrate such as a bandage, a soap base, a personal care product base, a hygienic cleaning solution base, an IV solution, a foam base, an oral composition, or an aerosol or nebulizer mist solution.

In another embodiment, the formulation according to the present invention is a shampoo composition, an animal cleaner composition, a detergent composition, a wipe, a soap composition, a foamed composition, a household cleaning composition, a personal care product composition, an ointment, a disinfectant coating, or an aresol, vapor or nebulizer composition.

The personal care product may be a deodorant, sunscreen lotion, cosmetic composition, soap, cleanser, toothpaste, or mouthwash.

The present invention also contemplates a method for cleaning a surface comprising the steps of:
applying an effective amount of the formulation of claim 1 to the surface to be treated;
optionally rubbing the formulation into the surface;
repeating steps a and b after a period of time.

The surface is chosen from an animal fur, human skin, human scalp, or a non-human surface.

The formulation may be a liquid, cream, ointment, emulsion, powder, lotion, IV solution, oral solution, mist, gel, solid, or spray form.

Furthermore, the formulation of the present invention, having a high purity rhamnolipid, may be used to clean, disinfect, or deodorize, by creating a non-stick film that prevents bacteria and fungus from adhering to surfaces being cleaned. In order to prevent the growth of bacteria and/or fungus, it is necessary for the he rhamnolipid to be either a Crude or Purified Rhamnolipid and contain either, a mono-rhamnolipid, a di-rhamnolipid, or a combination of the two.

DETAILED DESCRIPTION OF THE INVENTION

Rhamnolipid Purity

The formulations of the present invention may use crude or highly purified rhamnolipids. A crude rhamnolipid is a rhamnolipid, having many impurities both external impurities, and/or a variety of various Rhamnolipid mixtures, which causes a reduced effect on the formulation. Highly purified rhamnolipids is a rhamnolipid whose external impurities have been removed, and/or the Rhamnolipids have been purified to meet certain parameters to cause an increased effect on the formulation which includes di-rhamnolipid, mono-rhamnolipid or a certain mixture of both.

After long experimentation, and in contrast to the rhamnolipid formulations known in the art, the present inventor discovered that crude Rhamnolipids in the form readily available in the marketplace, and further refined or purified can be used in certain formulations of the present invention, while highly purified Rhamnolipids are required for certain other formulations.

The formulations are made by eliminating unwanted impurities from the initial mixture and then establishing the percentage and type of Rhamnolipid to be resident in the final mixture and simply diluting the rhamnolipid preparation with a carrier or diluents, preferably water or ethanol. The present invention is not limited by the use of water and ethanol as carrier or diluents. The present invention contemplates the use of any carrier or diluents, as long as it is compatible with rhamnolipid.

In general, the rhamnolipid preparation ("crude" or partially purified therefrom) is diluted to a final concentration of less than 70%. In various embodiments of the invention, the final formulations contain in the range of about 5% to about 70% rhamnolipid preparation, with preferred formulations being about 65%, or about 35%, or about 25%, or about 10% or about 5% or less of the rhamnolipid preparation in the final formulation.

In the present invention the use of the term "rhamnolipid" implies indistinctively crude or highly purified Rhamnolipids, and various mixtures of the Rhamnolipid components.

EXAMPLE 1

Rhamnolipids are secreted from *Pseudomonas aeruginosa*. Typically, the bacterium *Pseudomonas aeruginosa* is cultured in a suitable medium and grown to a desired density. The bacteria themselves are removed from the culture media by any method known in the art, such as centrifugation. The supernatant may be used directly as the crude preparation, or further processing steps well-known to those of skilled in the art may be carried out (e.g. concentration, filtration, column chromatography, and the like). Notably, however, the final rhamnolipid preparation is not highly purified and is referred to as "crude rhamnolipid", and typically contains a mixture of both mono-rhamnolipids and di-rhamnolipids, and other compounds. Those of skill in the art will recognize that the precise details of cultivation and partial purification may vary somewhat and still be within the scope of the invention.

Preparation of crude rhamnolipid preparations and highly purified rhamnolipid preparations may be prepared by methods that are well-known to those of skill in the art.

The formulations of the invention comprise one or more types of rhamnolipids. These rhamnolipids could be a mono-rhamnolipid, a di-rhamnolipid, or a combination of the two.

"Effective amount" means the amount of the rhamnolipid that as a whole, provides an antimicrobial (including, for example, antiviral, antibacterial, or antifungal) activity that reduces, prevents, or eliminates one or more species of microbes, such that an acceptable level of the microbe results. Typically, this is a level may be low enough not to cause clinical symptoms, and is desirably a non-detectable level. Formulations having Rhamnolipid for Animal Cleaning The present invention provides rhamnolipid based formulations and methods for their use in cleaning and deodorizing the skin and fur of animals.

After long experimentation, the present inventor discovered that rhamnolipids can be used in formulations for the cleaning and maintenance of the appearance of animal fur, hair, hide, and skin in a facile manner, and at the same time, clean and deodorize the skin and fur of animals without all the hazards of bathing the animal, and lastly can be used to clean the habitats (stalls, kennels, pens) and ancillary materials used by the animals (saddles, blankets, bridles, collars, etc.)

The formulations of the invention comprise one or more rhamnolipids. These rhamnolipids includes mono-rhamnolipid, a di-rhamnolipid, or a combination of the two.

The carrier of the present invention is chosen from: polyethylene glycol (PEG), Citric acid, water, sodium laureth sulfate, aloe, alcohol, glycerin, canola oil, petrolatum, sodium hydroxide, glyceryl stearate, potassium hydroxide, mineral oil, lanolin, stearic acid, glycol stearate, sodium chloride, cocoa butter, citric acid, sodium phosphate, xanthan gum, potassium laureth phosphate, poysorbate 20, Vitamin E, wax, silica, cyclopenta Siloxane, Titanium Dioxide, Propylene Glycol, Stedric Acid, talc, or a combination thereof.

In a preferable embodiment, the present invention contemplates using a formulation containing 5% of a crude, partially purified rhamnolipid preparation, using water as the first diluents/carrier and ethanol as a second diluents/carrier.

EXAMPLE 2

Animal Cleaning Formulations

Two large mixed breed dogs owned by a first individual and one ferret and two small dogs owned by a second individual were treated in the following manner: a 5% formulation of crude rhamnolipid preparation, as described in Example 1, was prepared. The rhamnolipid formulation was applied by spraying the formulation to the paws, all sides, and underneath the dogs, and up to about one inch of the leg, beyond the paw. The results were monitored over a period of two weeks. The results showed that the areas of the dogs' fur and skin to which the rhamnolipid formulation had been applied immediately assumed a shiny, clean, and odor free appearance which was distinctly improved in comparison to the fur and skin that was not treated.

When the formulations of the present invention were applied directly to the fur and skin of the animals, it resulted in a marked improvement in the appearance of the fur and skin of the animal. Hair and fur to which the formulations were applied showed an increased luster and shine, and remained odor free. This healthy, clean appearance was maintained for several weeks before a further application was necessary.

In view that rhamnolipids exhibit low toxicity, the ingestion of the formulation by the animal (e.g. by licking the fur) would not be harmful.

In addition, the present invention contemplates adding to the formulation of the present invention pet grooming agents that promote the growth of the animal hair. The pet grooming agents that condition or instill sheen in the fur are preferred. The grooming agent may be in the form of a resin, a wax, a liquid or combinations thereof. The grooming agent must be soluble in an aqueous base formulation, non-toxic, environmental and impart a desirable beneficial quality to the animal fur.

EXAMPLE 3

Pet Spray

One indoor and one outdoor stall that housed dogs were sprayed daily with a 50% concentration (50% water) of rhamnolipid. The spray was applied liberally, to the degree of soaking the entire stall floor to ceiling. The result after one week of application was an odorless, clean looking home for the pets. The odorless effect was due to the antimicrobial effect of rhamnolipid application to the enclosures.

Further, this effect was retained for several weeks, without further application of the spray. When essentially undiluted crude rhamnolipid preparation was employed, some reddening of the skin was observed.

The precise amount of the formulation that is applied to the animal varies, depending on diverse factors, and will be determined on a case by case basis by the user.

After long experimentation, the present inventor discovered than formulations having less than 70% purity of the rhamnolipid preparation are preferable for use with domestic pets. Further, factors such as the type of animal, and the extent to which the rhamnolipid preparation had been partially purified, affected the range of concentrations that are most desirable for a particular application.

Those skilled in the art will recognize from this disclosure that the rhamnolipid formulations of the invention may be used to clean and improve the appearance of the fur and skin of a wide variety of animals. Examples include but are not limited to: small animals that are typically domestic pets (e.g. dogs, cats, ferrets, guinea pigs, hamsters, mice, rats, birds, rabbits, and the like); larger domesticated and/or commercially raised animals (e.g. cows, horses, bison, mules, oxen, sheep, pigs, rabbits, donkeys, etc.); or animals in captivity, for example in zoos, wild life preserves, circuses, etc. (e.g. monkeys, gorillas, bears, etc.).

The formulations of the present invention can be utilized on any animal, preferably mammals, to enhance cleanliness and to impart a deodorizing effect to skin and/or fur, hide, hair, etc. While the formulations are primarily intended for use in non-human animals, humans may also benefit from use of the formulations.

In general, a formulation with a lower concentration of rhamnolipid preparation (e.g. about 0.01% to about 10%) is preferably used for smaller domestic animals, whereas a formulation of higher concentration (e.g. about 25% or higher) would be used for larger animals, such as livestock or horses.

The invention also provides methods of using the formulations described herein. Briefly, a formulation comprising rhamnolipid is applied to the skin or fur of the animal to be cleaned, for example, by spraying a film of the formulation over the fur and skin until a desired appearance is achieved. The formulation can also be rubbed into the skin and fur if desired, for example using a wipe or cream containing the formulation. In some instances, the formulations may be provided as a wash or rinse, incorporated into a soap or detergent base, in liquid or other form, as an ointment or powder, or supplied in a concentrated form for dilution by the end user.

One advantage of the present invention is that the cleaning and deodorizing effects are relatively long-lasting: the improved appearance of the skin and fur typically lasts for many days, or even for several weeks. The spray can then be reapplied as desired.

The rhamnolipid formulations of the present invention may be utilized in a variety of settings and circumstances, and by a variety of end users, for example, pet owners and caretakers of various domesticated or partially domesticated animals, people who work with animals in various professional capacities (e.g. veterinarians, groomers, breeders, caretakers at zoos, circuses, animal parks, etc.), and the like.

In addition, the formulation of the present invention having high purity rhamnolipid can be used to treat animals who have ringworm, roundworms, and hookworms, Foot and Mouth Disease, Bovine spongiform encephalopthy (BSE, mad cow disease) *Brucalla* Infection (brucellosis), *Campylobacter* Infection (campylobacteriosis), *Cryptosporidium* Infection (cryptosporidiosis), *Escherichia coli* Q Fever (*Coxiella burnetti*) Infection, Rabies, *Salmonella* Infection (salmonellosis), *Yersinia enterocolitica* (yersiniosis) *Baylisascaris* Infection (raccoon roundworm), *Brucella* Infection (brucellosis), A bacterial disease associated with bison, deer, and other wild animals. Giardia Infection (giardiasis) A parasitic disease associated with animals and their environment (including water). Hantavirus Pulmonary Syndrome (hantavirus): A rare viral disease associated with some types of wild mice. *Herpesvirus simiae* Infection (B virus): A deadly viral disease associated with macaque monkeys. *Histoplasma* Infection (histoplasmosis: A fungal disease associated with bat guano (stool). Lymphocytic Choriomeningitis: A viral disease associated with rodents and house mice. *Mycobacterium tuberculosis* Infection (TB): A bacterial disease associated with deer, elk, and bison.

Rhamnolipids in Personal Hygiene and Care Products

Furthermore, the present invention provides rhamnolipid formulations and methods for their use in personal hygiene and care products. Rhamnolipids act as an antimicrobial agent and a surfactant in personal care products.

EXAMPLE 4

Human Applications

The present inventor treated himself and other individuals with a shampoo comprising rhamnolipid in the following manner: a 2% formulation of crude rhamnolipid preparation, as described in Example 1 using water as the dilutant was prepared. The rhamnolipid was added to a shampoo base and applied by soaking the head of the individual with water and working it into a soapy lather and then left to sit on the hair for one minute. The formulation was then rinsed. The previous steps were repeated. The results were monitored over a period of three days until hair needed another cleaning. The results showed that the antimicrobial effect left the scalp free from odor for three days, while maintaining a luster.

When essentially undiluted crude rhamnolipid preparation was employed in an amount between 0.01% to 35% of the personal care product, some redness of the skin was observed. Thus, formulations of lower concentrations (e.g. less than about 70% of the crude rhamnolipid on the personal care product) are recommended for use on the body.

Furthermore, the present inventor applied a formulation comprising 70% rhamnolipid and 30% water into the scalp. The results showed that the antimicrobial effect of the rhamnolipid, even if used alone, left the scalp free from odor for three days, while maintaining a luster.

EXAMPLE 5

Hair Growth

Applicant notes that after one month of monitoring the scalp, the higher rhamnolipid formulations caused hair on the scalp to grow, whereas before application was administered, there was no hair present. Thus, rhamnolipids assisted in treating baldness.

Furthermore, Applicant noted that because of their detergent properties, and beneficial properties to the skin, bathing with rhamnolipids improves and maintains a clean appearance of the skin, and at the same time treats certain dry skin conditions and also acts as an antimicrobial agent. The use of rhamnolipid formulations simplifies the process of cleaning and maintaining hair, skin, finger, toenails and ears.

In a preferred embodiment of the invention, the formulations are provided and used as sprays, soaps, shampoo, creams, wash or rinse, incorporated into a "soap" or detergent base, in liquid, as a wipe permeated with the formulation, ointment or powder, or supplied in a concentrated form for dilution by the end user.

Those of skill in the art will recognize that other additives may also be added to the formulations for any of a variety of purposes, either in place of, or in addition to, another diluents. For example, agents that extend the shelf life of the formulations may be added. Among these, parabenzene is a preferred additive, since it is also known to be beneficial for the skin.

Other possible additives are, for example, fragrances known in the art such as phenyl ethyl alcohol.

Furthermore, the present invention contemplates adding vitamins, emulsifying agents, colorants, or the like, to achieve desirable cosmetic effects or otherwise enhance the value of the application.

Those of skill in the art will recognize from this disclosure that the rhamnolipid formulations of the invention may be used as a personal care application. Examples include but are not limited to: Infant wipes, facial wipes, body wipes, infant body and facial sprays. These also include soaps, shampoos, bath gels, body rinses, and sprays of the present invention that can be utilized on any person at any age, to enhance cleanliness as an antimicrobial agent and to impart a deodorizing effect to body parts such as skin, hair, finger and toenails, ears, etc. While the formulations are primarily intended for use in people, animal habitants may also benefit from use of the rhamnolipids.

Simply spraying or using rhamnolipids as a cleaner, deodorizer, and antimicrobial application will produce a healthier environment for domestic pets, livestock, and people. As a "clean room" application, a formulation of a rhamnolipid used as a nebulizer will act to clean and disinfect a room where certain procedures are required.

Rhamnolipid Formulations for Industrial Environment

EXAMPLE 6

Nebulizer Spray

An enclosed unit used for storage was equipped with a rotating fan and a nebulizer (we used a battery operated unit, silent. Off the shelf ultrasound model) to compress air and mixed rhamnolipid (65% rhamnolipid, 35% water) to deliver a wet mist into the unit continuously for one week.

The musty smell was completely neutralized and the dirty film located on the walls and ceiling dripped to the ground and was mopped up. The antimicrobial, antifungal properties of the mist did in fact reduce microorganism growth.

In regular nebulizer applications, about 0.01% to about 35% of rhamnolipid in the formulation is desirable. For sanitation purposes, at least 35% of rhamnolipid in the formulation is required.

The precise amount of the formulation that is applied to the surface is not crucial and will be determined on a case by case basis by the user of the formulation. One advantage of the present invention is that the cleaning and deodorizing effects are relatively long-lasting.

Formulations for Other Uses

These applications also target the medical industry, industrial and household items, when applied, will create a clean working surface. Applicant discovered that when the rhamnolipids formulation, according to the present invention, is applied onto a surface, it creates a bio-film on the surfaces that prevents the unwanted growth of microbes, bacteria and fungus.

The formulation of the present invention having a high purity rhamnolipid may be used to clean, disinfect, and deodorize, by creating a non-stick film that prevents bacteria and fungus from adhering to surfaces being cleaned. In order to prevent the growth of bacteria and/or fungus, it is necessary that the rhamnolipid be high purity (as defined herein) and contain a mono-rhamnolipid, a di-rhamnolipid, or a combination of the two.

The non-stick surface, or a layer of rhamnolipids, may be used to package medical tools, bandages, cleaning devices, household items, or coating of prosthesis, or other implants inserted into a human body through a medical operation, etc.

This technique is especially used to create a clean surface and then leave a film on the surface such that microbes and fungus do not stick to surfaces.

EXAMPLE 7

Antibotic/Anti-Fungal Coating

Because of the natural antibacterial and anti fungal effect of the rhamnolipids, the formulation of the present invention can be used to disinfect plastics, rubbers woods, and metals such as toothbrushes, hairbrushes, toys, kitchen appliances, or other food handling appliances and everyday products.

A rhamnolipid formulation (25% rhamnolipid, the rest water) was used to soak toothbrush holders, hair brushes, and infant plastic toys. The antimicrobial and surface tension properties of the rhamnolipid maintained a clean surface for at least a week.

Products manufactured with Rhamnolipid coatings will offer the same effect. With a higher purity of rhamnolipids included in the construction of the product or simply dipped or sprayed on the product, the effect is expected to last much longer than exhibited in the test and experimentation.

EXAMPLE 8

Consumer Household, Industrial, and Medical (Human or Veterinarian) Goods

Applicant noted that when goods were coated and packaged with a film, such as a plastic or rubber baby doll, including rhamnolipids, unwanted microbes that cause sickness were reduced.

EXAMPLE 9

Human Applications for Treating Vitiligo

Vitiligo is a pigmentation disorder in which melanocytes (the cells that make pigment) in the skin are destroyed. As a result, white patches appear on the skin in different parts of the body.

The formulation according to the present invention was applied to the skin of patients presenting signs of vitiligo. After several months of applying the formulation onto the skin of the patients, the present inventor noticed a remarkable reduction on the appearance of white patches with vitiligo.

EXAMPLE 10

Diapers

The present inventor discovered that the formulation according to this invention can be use in conjunction with disposable or non-disposable diapers for the protection of infants from microorganism, bacteria, and/or fungus and at the same time to protect and conditioning the skin of the infant.

The present invention contemplates three ways of incorporating the formulation including rhamnolipids into the diaper:

by spraying the skin of the baby with a spray containing the formulation, as described before;

rubbing the skin of the baby with a wipe containing the formulation as described before; or incorporating an effective concentration of the formulation of the present invention to a woven or non-woven cellulose-containing substrate, such as a moisture absorbent fabric of the type commonly used for diapers. Such fabrics are well known in the art, and any suitable such material may be used, including those containing super absorbent materials.

For the purpose of applying these agents to combat germs, bacteria, fungus, and bad odor in infant diapers, it was determined that directly incorporating them into the fabric of the diaper, or into the liquid present in a wet wipe to be used for cleansing of the infant, offered the greatest advantages. Various methods are known in the art for the application of liquid compositions to absorbent fabrics, and such methods are not considered as part of the present invention.

The present invention is related to the selection of the specific rhamnolipid formulation used, provided that sufficient amount of the formulation is integrated to the diaper as to be an effective antimicrobial composition when in contact with a site subject to microbial growth.

EXAMPLE 11

Wound Healing on Animals

Mice presenting skin lesions including active inflammation, ulceration, dermal fibrosis, parakeratosis, cyst, or surface hemorrhage, were directly treated by applying a formulation containing rhamnolipid into the wounds. The skin lesions were still apparent, but appeared to be healing, on day 14. Treatment was continued until complete healing of the skin lesions was observed.

Those of skill in the art will recognize that other additives may also be added to the Rhamnolipid formulations to increase the effectiveness of the overall product, or process.

What is claimed is:

1. A method for applying a non-stick film over a surface, said method comprising, applying onto the surface an effective amount of a formulation comprising:
   a) at least 25% of a rhamnolipid, wherein the rhamnolipid is at least one of a mono-rhamnolipid or a di-rhamnolipid, and the rhamnolipid has a purity of at least 90%; and
   b) a carrier selected from the group consisting of polyethylene glycol, silica, and a mixture of water and ethanol.

2. The method according to claim 1, wherein the formulation is applied to the surface by spray, mist, dipping, direct pour, foam, or wiping the formulation onto the surface.

3. The method according to claim 1, wherein the surface is selected from the group consisting of a fabric substrate, a non-fabric substrate, a woven substrate, a non-woven cellulose-containing substrate, a furniture, medical devices, food preparation devices, toys, or personal hygienic devices.

* * * * *